US00PP31310P2

(12) United States Plant Patent
Hartman

(10) Patent No.: US PP31,310 P2
(45) Date of Patent: Dec. 31, 2019

(54) ***CALADIUM* PLANT NAMED 'KAT 011-118'**

(50) Latin Name: ***Caladium* X *hortulanum***
Varietal Denomination: KAT 011-118

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/350,105

(22) Filed: Sep. 25, 2018

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373, 263.1

CPC ... A01H 5/12; A01H 5/02; A01H 5/00; A01H 6/00
See application file for complete search history.

(56) References Cited

U.S. PATENT DOCUMENTS

PP27,096 P2 * 8/2016 Hartman ..... A01H 5/02 Plt./373

* cited by examiner

*Primary Examiner* — June Hwu
(74) *Attorney, Agent, or Firm* — C. A. Whealy

(57) ABSTRACT

A new and distinct cultivar of *Caladium* plant named 'KAT 011-118', characterized by its intermediate height; upright and mounding plant habit; dense and bushy appearance; vigorous growth habit and rapid growth rate; fancy-type leaves that are dark green in color with bright red-colored centers and venation that resist fading; and petioles that are dark brown in color with greenish greyed orange-colored streaks and greenish brown stipples, streaks and tessellations.

4 Drawing Sheets

Botanical designation: *Caladium* X *hortulanum*.
Cultivar denomination: 'KAT 011-118'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'KAT 011-118'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium* X *hortulanum* 'Frieda Hemple', not patented, as the female, or seed, parent with *Caladium* X *hortulanum* 'White Wonder', disclosed in U.S. Plant Pat. No. 21,044, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'KAT 011-118'. These characteristics in combination distinguish 'KAT 011-118' as a new and distinct *Caladium* plant:

1. Intermediate in height and upright and mounding plant habit; dense and bushy appearance.
2. Vigorous growth habit and rapid growth rate.
3. Fancy-type leaves that are dark green in color with bright red-colored centers and venation that resist fading.
4. Petioles that are dark brown in color with greenish greyed orange-colored streaks and greenish brown stipples, streaks and tessellations.

Plants of the new *Caladium* differ primarily from plants of the female parent, 'Frieda Hemple', in leaf color as leaves of the new *Caladium* are dark green in color with bright red-colored centers and venation whereas leaves of 'Frieda Hemple' are medium green in color with deep red-colored centers and venation.

Plants of the new *Caladium* differ primarily from plants of the male parent, 'White Wonder', in the following characteristics:

1. Plants of the new *Caladium* have fancy-type leaves whereas plants of 'White Wonder' have lance-type leaves.
2. Plants of the new *Caladium* and 'White Wonder' differ in leaf color as leaves of the new *Caladium* are dark green in color with bright red-colored centers and venation whereas leaves of 'White Wonder' are white to grey-green in color with light pink to white-colored venation and dark green-colored borders.

3. Plants of the new *Caladium* and 'White Wonder' differ in leaf petiole color as petioles of the new *Caladium* are dark brown in color with greenish greyed orange-colored streaks and greenish brown stipples, streaks and tessellations whereas petioles of 'White Wonder' are greenish tan with darker-colored stripes.

Plants of the new *Caladium* can be compared to plants of *Caladium* X *hortulanum* 'Kathleen', not patented. In side-by-side comparisons, plants of the new *Caladium* differ primarily from plants of 'Kathleen' in the following characteristics:

1. Plants of the new *Caladium* are shorter than plants of 'Kathleen'.
2. Plants of the new *Caladium* and 'Kathleen' differ in leaf color as leaves of the new *Caladium* are dark green in color with bright red-colored centers and venation whereas leaves of 'Kathleen' have medium green-colored margins and reddish pink-colored centers that fade to light pink with development.
3. Plants of the new *Caladium* and 'Kathleen' differ in leaf petiole color as petioles of the new *Caladium* are dark brown in color with greenish greyed orange-colored streaks whereas petioles of 'Kathleen' are greenish tan tinged with pinkish tan in color with greenish brown-colored stipples, streaks and stripes.

Plants of the new *Caladium* can be compared to plants of *Caladium* X *hortulanum* 'Rose Glow', disclosed in U.S. Plant Pat. No. 20,070. In side-by-side comparisons, plants of the new *Caladium* differ primarily from plants of 'Rose Glow' in the following characteristics:

1. Plants of the new *Caladium* and 'Rose Glow' differ in leaf color as leaves of the new *Caladium* are dark green in color with bright red-colored centers and venation whereas leaves of 'Rose Glow' are red purple in color with white-colored midveins, green-colored borders and dark green-colored margins.
2. Plants of the new *Caladium* and 'Rose Glow' differ in leaf petiole color as petioles of the new *Caladium* are dark brown in color with greenish greyed orange-colored streaks whereas petioles of 'Rose Glow' are greenish tan in color with darker green-colored tessellations and speckles.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'KAT 011-118' in a container and grown in a shadehouse (tuber de-eyed).

The photograph at the top of the second sheet is a comparison view of typical potted plants of the female parent, 'Frieda Hemple' (left), 'KAT 011-118' (center) and the male parent, 'White Wonder' (right).

The photograph at the bottom of the second sheet is a comparison view of typical potted plants of 'Kathleen' (left), 'KAT 011-118' (center) and 'Rose Glow' (right).

The photograph at the top of the third sheet is a comparison view of typical plants of 'KAT 011-118' grown in containers; the plant on the left has not had its tuber de-eyed and the plant on the right has had its tuber de-eyed prior to planting.

The photograph at the bottom of the third sheet is a side perspective view of typical plants of 'KAT 011-118' grown in an open production field.

The photograph at the top of the fourth sheet is a close-up view of typical freshly-harvested tubers with roots and leaf petioles of 'KAT 011-118'.

The photograph at the bottom of the fourth sheet is a close-up view of a typical inflorescence of 'KAT 011-118'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were eight weeks old and plants grown in the outdoor nursery were six months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'KAT 011-118'.

Parentage:

*Female, or seed, parent.*—*Caladium* X *hortulanum* 'Frieda Hemple', not patented.

*Male, or pollen, parent.*—*Caladium* X *hortulanum* 'White Wonder', disclosed in U.S. Plant Pat. No. 21,044.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments irregular elliptic to ovate in shape. Height: About 3 cm to 3.8 cm. Diameter: About 5.5 cm to 7 cm. Segment height: About 2.1 cm to 3.8 cm. Segment diameter: About 2.3 cm to 2.6 cm. Axillary bud size: About 3 mm by 5 mm. Texture: Thick, starchy; somewhat brittle. Color: Epidermis, freshly-harvested: Close to 164D, 158D and 159C. Epidermis, dried: Close to 200A to 200B. Cortical tissue: Close to 2D and 4C. Axillary buds: Close to N155C, N155D and 49D. Root description: Thick, fleshy contractile roots with few lateral branches; color, close to 155C and N155D. Rooting habit: Dense, profuse.

Plant description:

*Plant type*.—Herbaceous perennial; suitable as a potted plant in containers 15-cm to 25-cm and suitable as a landscape plant in shaded areas.

*Plant and growth habit*.—Intermediate in height and upright to mounded plant habit; dense and bushy appearance; vigorous growth habit and rapid growth rate; potted plants finish in saleable form in about seven weeks after planting tubers; leaf petioles and leaves arise from one or more growing points on tubers; leaf petioles initially upright and outwardly leaning to arching with development.

*Plant height, from soil level to top of foliar plane, shadehouse-grown potted plants*.—About 28 cm to 34 cm.

*Plant height, from soil level to top of inflorescences, shadehouse-grown potted plants*.—About 37 cm.

*Plant diameter or spread, shadehouse-grown potted plants*.—About 40 cm to 47 cm.

*Number of shoots per plant, shadehouse-grown potted plants, tubers not de-eyed*.—About three develop per #1 tuber.

*Number of shoots per plant, shadehouse-grown potted plants, tubers de-eyed*.—About four develop per #1 tuber.

*Cataphylls, shadehouse-grown potted plants*.—Length: About 4.8 cm to 7.5 cm. Width: About 1.2 cm to 1.7 cm. Shape: Narrowly elliptic. Apex: Acute. Base: Sheathing the stem. Color, inner surface: Close to N155B; colors and patterns on the outer surface are visible on the inner surface. Color, outer surface: Close to N155C and N170D, densely and variably streaked, stippled and mottled with close to 200A tinged with close to 147A; with development, color becoming closer to 200B and 200D stained with close to 187A.

Leaf description:

*Arrangement and type*.—Alternate; simple; fancy-type.

*Length, shadehouse-grown potted plants*.—About 16.5 cm to 23 cm.

*Width, shadehouse-grown potted plants*.—About 12 cm to 15.2 cm.

*Shape*.—Broadly ovate.

*Apex*.—Acuminate.

*Base*.—Sagittate to peltate.

*Margin*.—Entire; mostly flat with some broad undulations.

*Texture and luster, upper surface*.—Smooth, glabrous; dull sheen.

*Texture and luster, lower surface*.—Smooth, glabrous; glaucous with a dull sheen.

*Venation pattern*.—Pinnate.

*Color, shadehouse-grown potted plants*.—Developing and fully developed leaves, upper surface: Background color: Darker than 137A tinged with close to 139A. Leaf edge: Close to 187B. Basal notch: Close to 187B. Midvein: Close to 53B and 53C. Primary venation: Close to 183A tinged with close to 53A. Lateral venation: Close to 183A tinged with close to 53A to 53B. Interveinal areas: Close to 53D tinged with close to 51B to 51C. Developing and fully developed leaves, lower surface: Background color: Close to 191A tinged with close to 189A. Leaf edge: Close to 187B. Basal notch: Close to 187A to 187B. Midvein: Close to 185C streaked with close to 185B. Primary venation: Close to 182B to 182C. Lateral venation: Close to 182D tinged with close to 177D and faint flecks, close to 177B to 177C. Interveinal areas: Close to 185C and 185B to 185C.

*Petioles*.—Aspect: Initially upright and straight and outwardly leaning and arching with development; flexible. Length, shadehouse-grown potted plants: About 19 cm to 29 cm. Diameter, distally, shadehouse-grown potted plants: About 4 mm to 4.5 mm. Diameter, proximally, shadehouse-grown potted plants: About 7 mm to 9.5 mm. Texture: Smooth, glabrous. Color, shadehouse-grown potted plants: When developing and fully developed: Close to 200A and 202A variably streaked with close to N170D or N170D tinged with close to 147B to 147C, stippled, streaked and tessellated with close to 200C tinged with close to 147B; distally, close to 182C and 181C variably streaked and stippled with close to 200C or striped with close to 200A. Wing length, shadehouse-grown potted plants: About 5.5 cm to 7 cm. Wing diameter, shadehouse-grown potted plants: About 8 mm to 10 mm. Texture and luster, inner and outer surfaces: Smooth, glabrous; dull. Wing color, shadehouse-grown potted plants: Inner surface: Close to N155A; colors and patterns on the outer surface are visible on the inner surface. Outer surface: Close to N155C and N170D densely and variably streaked, stippled and mottled with close to 200A tinged with close to 147B.

Inflorescence description: Inflorescences observed on nine week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring in central Florida; flowers develop about nine weeks after growth commences; inflorescences last about three days before fading; inflorescences persistent.

*Spathe*.—Length, overall: About 12 cm. Length, distal open portion: About 7.6 cm. Length, proximal closed portion: About 4.4 cm. Width, distal open portion: About 5.5 cm. Depth, distal open portion: About 2.6 cm. Width, at constriction: About 1.7 cm. Width, proximal closed portion: About 2.7 cm. Shape, open portion: Ovate to elliptic to slightly obovate. Apex: Acuminate. Base: Obtuse. Margin: Entire; smooth; distally, slightly recurved. Texture and luster, front surface: Smooth, glabrous; dull. Texture and luster, rear surface: Smooth, glabrous; dull, glaucous. Color, front surface: Distal open portion: Close to 155C tinged with close to 145D; with development, color becoming closer to N199B. Proximal closed portion: Close to 147D; distally faintly tinged and flecked with close to N186C; color does not change with development. Color, rear surface: Distal open portion: Close to 145D; margins tinged with close to 155C; color does not change with development. Proximal closed portion: Close to 194A, 147C to 147D and 146D; random areas, close to 155A; color does not change with development.

*Spadix*.—Length, overall: About 6.9 cm. Length, male flower zone: About 4.9 cm. Length, sterile zone: About 1 cm. Length, female flower zone: About 1 cm. Diameter, male flower zone: About 9 mm. Diameter, sterile flower zone: About 6 mm. Diameter, female flower zone: About 7 mm. Shape: Columnar, spindle-shaped. Apex: Acute. Base: Obtuse. Aspect: Upright. Color, mature, male zone: Close to 145D and 150D. Color, mature, sterile zone: Close to 159C. Color, mature, female zone: Close to 155C and 155D. Male flowers: Quantity per spadix: About 189. Shape: Obovate. Height: About 3 mm. Diameter: About 3 mm. Pollen amount: Moderate. Pollen color: Close to 4C. Female flowers: Quantity per spadix: About 96. Shape: Obovate. Height: About 3 mm. Diameter: About 2.2 mm. Stigma color: Close to 155C. Ovary color: Close to 155D.

*Scape*.—Length: About 25 cm. Diameter: About 7 mm. Strength: Sturdy; flexible. Aspect: Mostly erect. Texture and luster: Smooth, glabrous; dull, glaucous. Color: Close to N170D and 159C stippled, streaked, tessellated and striped with close to 200C to 200D tinged with close to 147B.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'KAT 011-118' as illustrated and described.

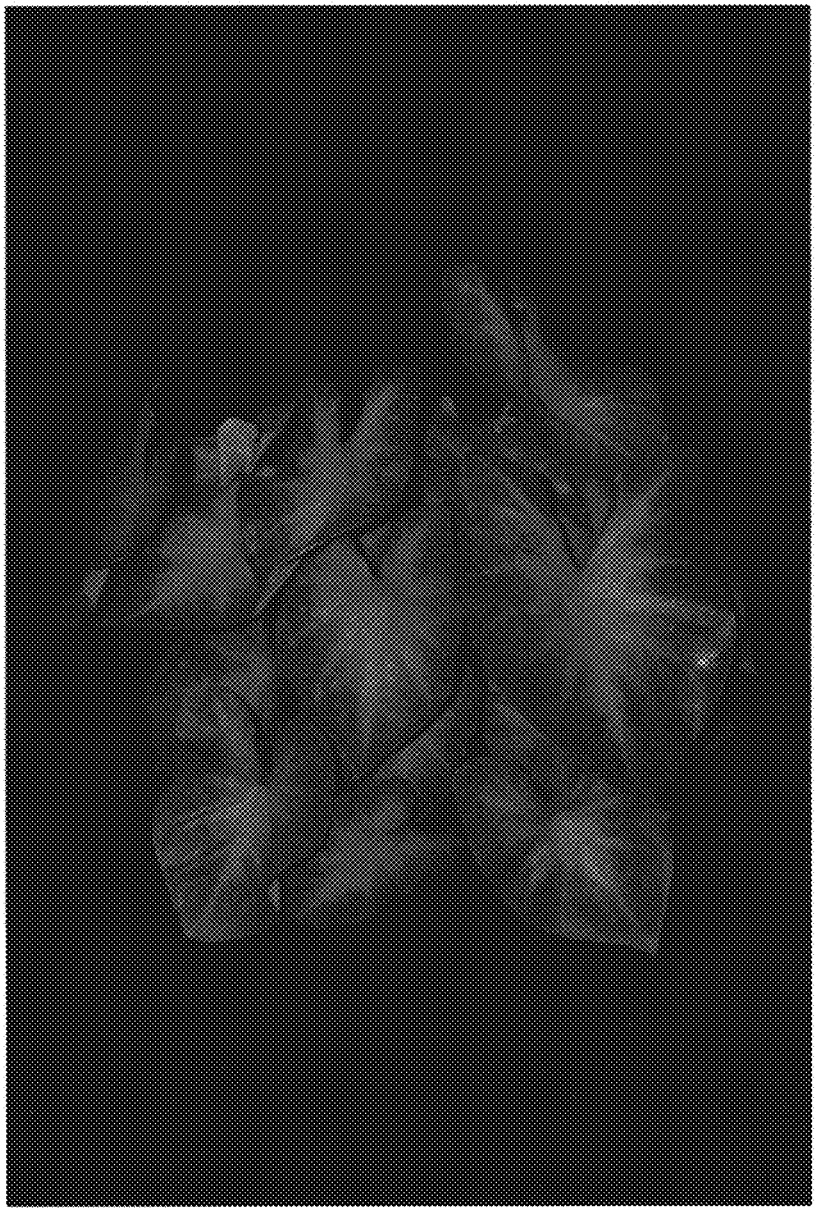

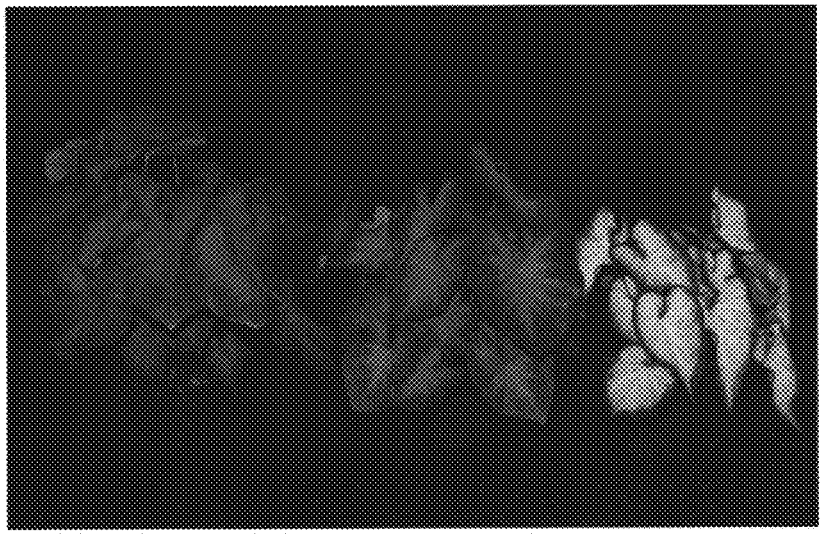
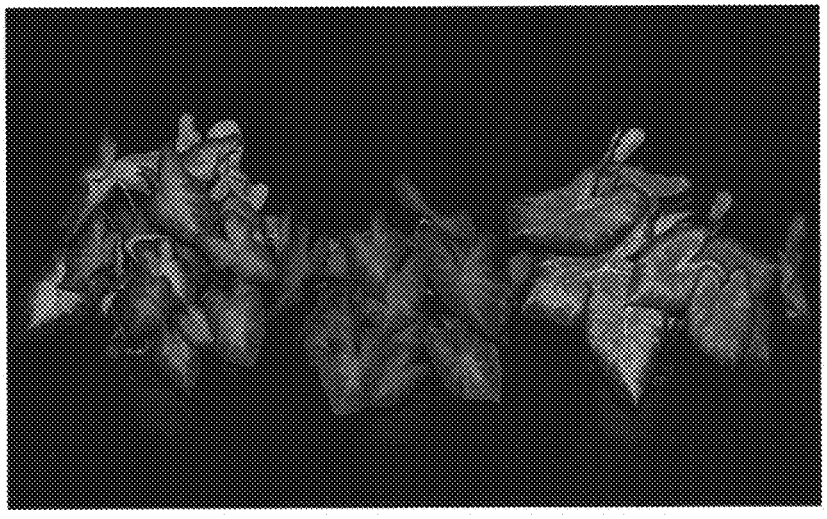

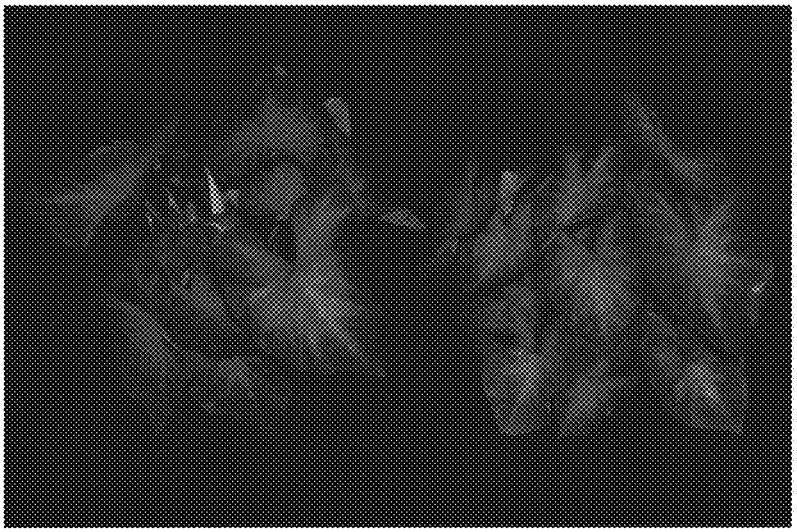
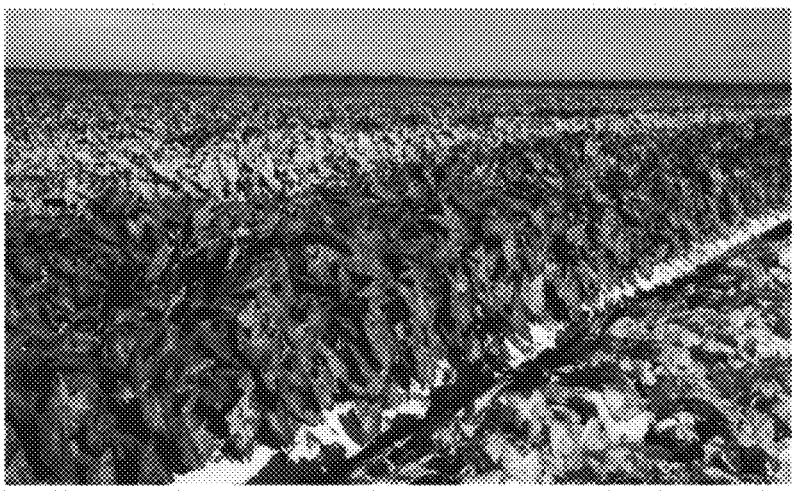

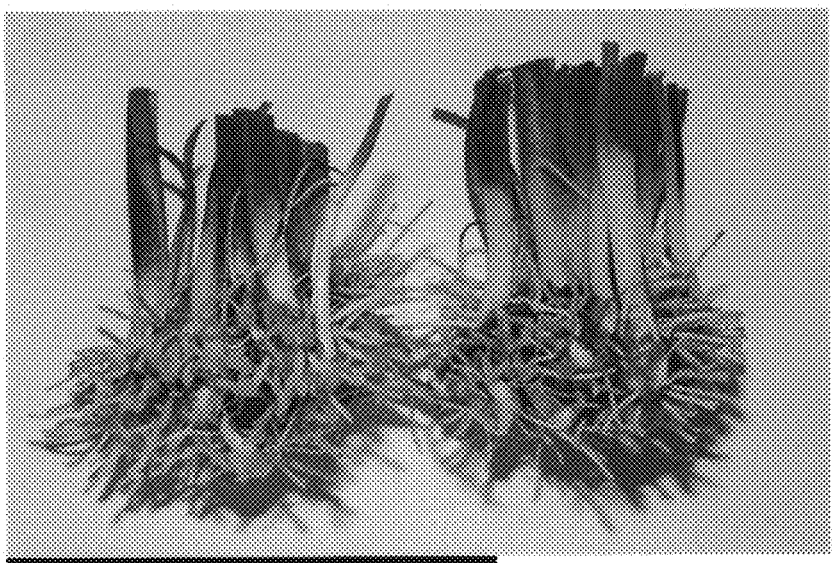
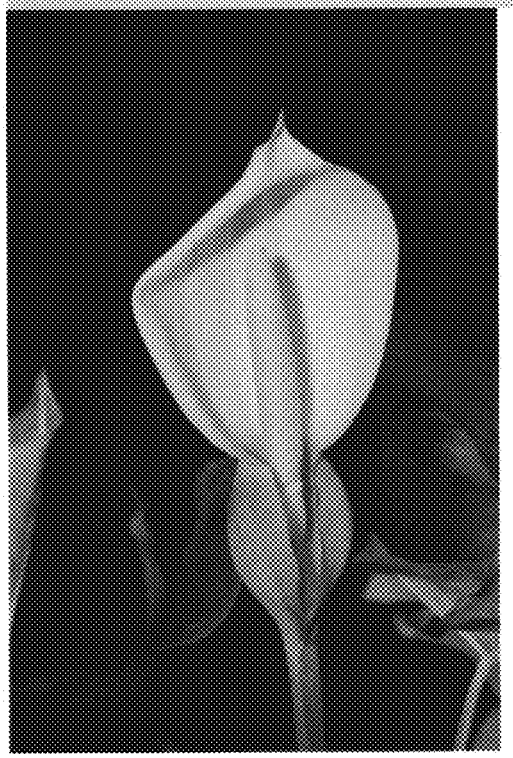

* * * * *